United States Patent
Satoh (10) Patent No.: US 8,282,551 B2
(45) Date of Patent: Oct. 9, 2012

(54) ULTRASONIC DIAGNOSTIC APPARATUS, DATA ANALYSIS METHOD, AND DATA ANALYSIS PROGRAM

(75) Inventor: Yoshiaki Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1085 days.

(21) Appl. No.: 11/954,512

(22) Filed: Dec. 12, 2007

(65) Prior Publication Data

US 2008/0146929 A1    Jun. 19, 2008

(30) Foreign Application Priority Data

Dec. 13, 2006    (JP) .................... 2006-335593

(51) Int. Cl.
    *A61B 8/00* (2006.01)
(52) U.S. Cl. .............. 600/437; 600/438; 600/443
(58) Field of Classification Search ............... 600/437, 600/438, 443
    See application file for complete search history.

(56) References Cited

U.S. PATENT DOCUMENTS

2006/0079777 A1*    4/2006    Karasawa .............. 600/443

FOREIGN PATENT DOCUMENTS

| JP | 2001238884 A | 9/2001 |
| JP | 2003-061964 A | 3/2003 |
| JP | 2004-041617 A | 2/2004 |
| JP | 2004321582 A | 11/2004 |

OTHER PUBLICATIONS

Yamaguchi et al., Estimation of Characteristics of Echo Envelope Using RF Echo Signal From the Liver, 2001, Japanese Journal of Applied Physics, vol. 40, pp. 3900-3904.*
Ito et al. "Quantitative Evaluation of Diagnostic Information Around the Contours in Ultrasound Images."2005. J Med Ultrasonics. vol. 32, pp. 135-144.*
Naohisa Kamiyama, et al., "Tissue Characterization Using Statistical Information from Ultrasound Echo Signals", Medical Imaging Technology, Mar. 2003, pp. 112-116, vol. 21, No. 2.
Yasutomo Fujii, et al., "Texture Analysis with the New Method of Segments the Region of Interest into Multiple Layers for RF Amplitude Histogram Analysis in the Fibrous Liver of Rats", J Med Ultrasonics, 2001, pp. J681-J691, vol. 28, No. 4.
Japanese Office Action corresponding to Japanese Patent Application No. 2006-335593, dated Oct. 3, 2011.

* cited by examiner

Primary Examiner — James Kish
(74) Attorney, Agent, or Firm — Sughrue Mion, PLLC (57) ABSTRACT

An ultrasonic diagnostic apparatus in which a speckle analysis can be made in a simple manner and an analysis result can be promptly displayed. The ultrasonic diagnostic apparatus includes: a transmitting and receiving unit for converting reception signals into digital signals; a signal processing unit for generating envelope data based on the digital signals; an image data generating unit for generating image data based on the envelope data; a speckle analysis unit for generating speckle analysis result data based on the envelope data; a display unit for displaying an ultrasonic image and a corresponding speckle analysis result; and a ROI setting unit for setting a ROI in the ultrasonic image; wherein the speckle analysis unit includes a memory for storing the envelope data, and a computation part for generating the speckle analysis result data based on the envelope data corresponding to the set ROI.

12 Claims, 5 Drawing Sheets

ULTRASONIC DIAGNOSTIC APPARATUS, DATA ANALYSIS METHOD, AND DATA ANALYSIS PROGRAM

CROSS-REFERENCE TO RELATED APPLICATION

The present application claims priority from Japanese Patent Application No. 2006-335593 filed on Dec. 13, 2006, the contents of which are incorporated herein by reference in their entirety.

BACKGROUND OF THE INVENTION

1. Field of the Invention

The present invention relates to an ultrasonic diagnostic apparatus for transmitting and receiving ultrasonic waves to perform imaging of organs and so on within a living body and generating ultrasonic images to be used for diagnoses. Furthermore, the present invention relates to a data analysis method and a data analysis program for performing analysis of data obtained in the ultrasonic diagnostic apparatus.

2. Description of a Related Art

In an ultrasonic diagnostic apparatus used for medical purposes, an ultrasonic probe is typically used to scan an object to be inspected with an ultrasonic beam formed by synthesizing plural ultrasonic waves and receive ultrasonic echoes reflected within the object, and thereby, image information on tissues of the object is obtained based on the intensity of the ultrasonic echoes. According to the ultrasonic diagnostic apparatus, a living body is acoustically measured by utilizing ultrasonic waves, and therefore, tissue properties of organs within the living body can be noninvasively diagnosed.

For example, the tissue property diagnosis of liver using the ultrasonic diagnostic apparatus enables early detection of cirrhosis. The cirrhosis refers to a symptom in which destruction and reproduction of liver cells are repeated and fibrillated tissues are increased within the liver and the liver is hardened and reduced. In this case, a feature appears in the intensity pattern of ultrasonic echoes in an ultrasonic image of the liver, and thus, the progression of the cirrhosis symptom can be visually confirmed.

Sometimes, the tissue property diagnosis using the ultrasonic diagnostic apparatus is made based on the pattern of speckles that appear due to mutual interference of echo signals reflected by a number of minute scatterers. For example, in the case where the liver is in the normal condition, the speckle pattern in the ultrasonic image is homogeneous. On the other hand, in the case where the liver is in the worsening cirrhosis symptom, the speckle pattern in the ultrasonic image is inhomogeneous. However, the visual evaluation largely depends on the experience of a person who makes a diagnosis, and therefore, quantitative evaluation is desired for homogeneousity of speckle pattern using the statistical nature of speckle pattern.

Naohisa KAMIYAMA et al., "Tissue Characterization Using Statistical Information from Ultrasound Echo Signals", MEDICAL IMAGING TECHNOLOGY, Vol. 21, No. 2, March 2003, pp. 112-116 discloses a study on tissue property diagnosis using speckle patterns obtained by an ultrasonic diagnostic apparatus. According to KAMIYAMA et al., generally, the echo signal status from numerous random scatterers is expressed as a probability density distribution function and a liver condition can be diagnosed based on whether or not the probability density distribution function is distributed along a Rayleigh distribution. KAMIYAMA et al. also discloses that such a statistical technique is realized as an image filter.

Further, Yasutomo FUJII et al., "Texture Analysis with the New Method of Segments the Region of Interest into Multiple Layers for RF Amplitude Histogram Analysis in the Fibrous Liver of Rats", J Med Ultrasonics, Vol. 28, No. 4, 2001, pp. J681-J691 discloses that, utilizing the fact that the histogram of enveloped-amplitude of RF (radio frequency) signals obtained from a homogeneous scattering medium resembles a Rayleigh distribution, a histogram analysis of enveloped-amplitude of RF signals is performed by focusing on the feature of the Rayleigh distribution function and segmenting ROI (Region of interest).

Furthermore, as a technology related to tissue property diagnosis using an ultrasonic diagnostic apparatus, Japanese Patent Application Publication JP-P2003-61964A discloses an ultrasonic diagnostic apparatus including analyzing and operating means for extracting a specific signal by using the statistical nature of intensity or amplification information of echo signals generated from a part of an object to be inspected, and display means for displaying a result extracted from the analyzing and operating means. According to the ultrasonic diagnostic apparatus, not only the progression of cirrhosis, but also a minute abnormal lesion in the homogeneous tissue structure can be observed by smoothing images by using the statistical nature of speckle pattern and extracting minute structures.

Further, Japanese Patent Application Publication JP-P2004-41617A discloses an ultrasonic diagnostic apparatus including image forming means for forming ultrasonic images based on echo data obtained by transmission and reception of ultrasonic waves, binarizing means for generating plural binarized images by binarizing the ultrasonic images while varying threshold levels, region counting means for performing labeling processing with respect to each binarized image to obtain the number of independent regions with high brightness or low brightness, and graph creating means for creating a speckle evaluation graph showing the number of independent regions with respect to each threshold level. According to the ultrasonic diagnostic apparatus, it is described that, utilizing the phenomenon that appearance of speckles or speckle pattern differs depending on tissue properties, tissue diagnoses can be made.

The tissue property diagnosis of liver, etc. may be made in a medical checkup, for example, and it is desirable that the evaluation result can be acquired in a short time period. Further, it is desirable for the person who makes a diagnosis or the person to be examined to easily understand the acquired evaluation result. However, the signal processing in the technology disclosed in the above documents is extremely complicated, and it is difficult to acquire the evaluation result in a short time period. Further, it is difficult for the persons to easily understand the evaluation result.

SUMMARY OF THE INVENTION

The present invention has been achieved in view of the above-mentioned problems. A purpose of the present invention is to provide an ultrasonic diagnostic apparatus in which a speckle analysis can be made in a simple manner by using information obtained based on echo signals and an analysis result can be promptly displayed.

In order to accomplish the above-mentioned purpose, an ultrasonic diagnostic apparatus according to one aspect of the present invention includes: a transmitting and receiving unit for supplying drive signals to plural ultrasonic transducers respectively to transmit ultrasonic waves and converting reception signals, which are respectively outputted from the plural ultrasonic transducers receiving ultrasonic echoes, into digital signals; signal processing means for performing reception focus processing and envelope detection processing on the digital signals to sequentially generate envelope data; a storage unit for storing the envelope data for at least one frame generated by the signal processing means; image data generating means for generating image data representing an ultrasonic image based on the envelope data supplied from the signal processing means or the storage unit; speckle analyzing means for generating speckle analysis result data representing a speckle analysis result based on the envelope data supplied from the signal processing means or the storage unit; display means for displaying the ultrasonic image and the corresponding speckle analysis result on a display unit based on the image data generated by the image data generating means and the speckle analysis result data generated by the speckle analyzing means; and ROI (region of interest) setting means to be used for setting a ROI in the ultrasonic image displayed on the display unit; wherein the speckle analyzing means includes a memory for storing the envelope data for at least one frame, and computing means for generating the speckle analysis result data based on the envelope data corresponding to the ROI set by using the ROI setting means among the envelope data stored in the memory.

Further, a data analysis method according to one aspect of the present invention is a method to be used in an ultrasonic diagnostic apparatus for supplying drive signals to plural ultrasonic transducers respectively to transmit ultrasonic waves and converting reception signals, which are respectively outputted from said plural ultrasonic transducers receiving ultrasonic echoes, into digital signals, and the method includes the steps of: (a) performing reception focus processing and envelope detection processing on the digital signals to sequentially generate envelope data; (b) storing the envelope data for at least one frame generated at step (a) in a storage unit; (c) generating image data representing an ultrasonic image based on the envelope data generated at step (a) or stored in the storage unit at step (b); (d) displaying the ultrasonic image on a display unit based on the image data generated at step (c); (e) setting a ROI (region of interest) in the ultrasonic image displayed on the display unit; (f) storing the envelope data for at least one frame in a memory and generating speckle analysis result data representing a speckle analysis result based on the envelope data corresponding to the ROI set at step (e) among the envelope data stored in the memory; and (g) displaying the ultrasonic image and the corresponding speckle analysis result on the display unit based on the image data generated at step (c) and the speckle analysis result data generated at step (f).

Furthermore, a data analysis program according to one aspect of the present invention is a program embodied on a computer readable medium to be used in an ultrasonic diagnostic apparatus for supplying drive signals to plural ultrasonic transducers respectively to transmit ultrasonic waves and converting reception signals, which are respectively outputted from said plural ultrasonic transducers receiving ultrasonic echoes, into digital signals, and the program actuates a CPU to execute the procedures of: (a) performing reception focus processing and envelope detection processing on the digital signals to sequentially generate envelope data; (b) storing the envelope data for at least one frame generated at procedure (a) in a storage unit; (c) generating image data representing an ultrasonic image based on the envelope data generated at procedure (a) or stored in the storage unit at procedure (b); (d) displaying the ultrasonic image on a display unit based on the image data generated at procedure (c); (e) setting a ROI (region of interest) in the ultrasonic image displayed on the display unit in accordance with operation of an operator; (f) storing the envelope data for at least one frame in a memory and generating speckle analysis result data representing a speckle analysis result based on the envelope data corresponding to the ROI set at procedure (e) among the envelope data stored in the memory; and (g) displaying the ultrasonic image and the corresponding speckle analysis result on the display unit based on the image data generated at procedure (c) and the speckle analysis result data generated at procedure (f).

According to the present invention, by generating the speckle analysis result based on the envelope data corresponding to the set ROI among the envelope data stored in the memory, the speckle analysis can be performed in the simple manner by using the information obtained based on the echo signals and the analysis result can be promptly displayed.

BRIEF DESCRIPTION OF THE DRAWINGS

FIGS. 6A-6C show the first to third examples of the speckle analysis result, respectively.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted.

Figure 1:
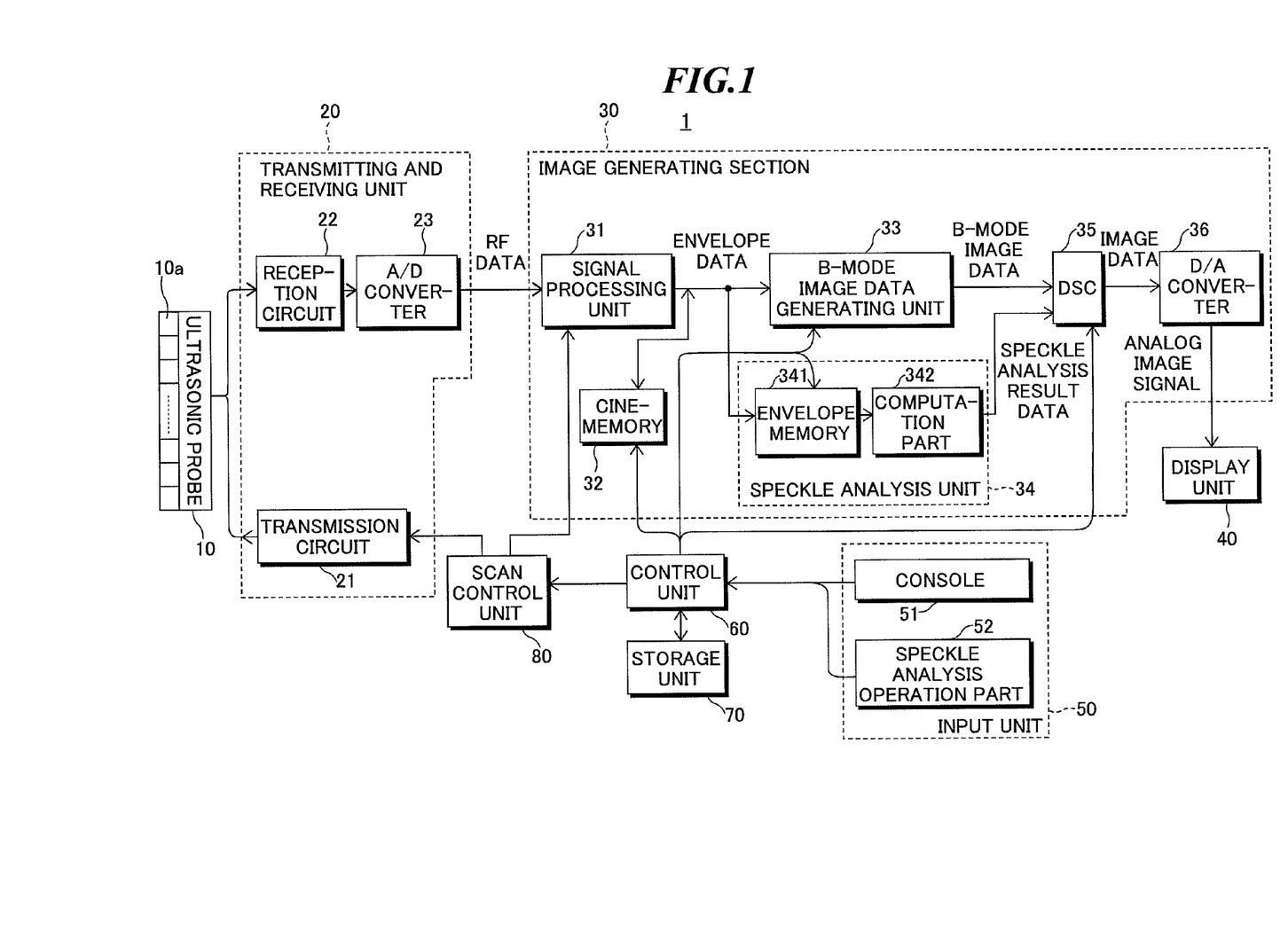
FIG. 1 is a block diagram showing a configuration of an ultrasonic diagnostic apparatus according to the first embodiment of the present invention.

FIG. 1 is a block diagram showing a configuration of an ultrasonic diagnostic apparatus according to the first embodiment of the present invention. An ultrasonic diagnostic apparatus 1 includes an ultrasonic probe 10, a transmitting and receiving unit 20, an image generating section 30, a display unit 40, an input unit 50, a control unit 60, a storage unit 70, and a scan control unit 80.

The ultrasonic probe 10 may be a probe of convex type, linear scan type, or sector scan type for use in contact with an object to be inspected, a probe of transesophageal type, or an ultrasonic endoscope of mechanical radial type or electronic radial type. The ultrasonic probe 10 includes plural ultrasonic transducers 10a that form a one-dimensional or two-dimensional transducer array. The ultrasonic transducers 10a transmit ultrasonic beams to the object based on applied drive signals, and receive ultrasonic echoes reflected from the object to output reception signals.

Each ultrasonic transducer is configured by a vibrator in which electrodes are formed on both ends of a material having a piezoelectric property (piezoelectric material) such as a piezoelectric ceramic represented by PZT (Pb(lead) zirconate titanate), a polymeric piezoelectric element represented by PVDF (polyvinylidene difluoride), or the like. When a voltage is applied to the electrodes of the vibrator by outputting pulse or continuous wave electric signals, the piezoelectric material expands and contracts. Due to the expansion and contraction, pulse or continuous ultrasonic waves are generated from the respective vibrators, and an ultrasonic beam is formed by synthesizing these ultrasonic waves. Further, the respective vibrators expand and contract by receiving propagating ultrasonic waves and generate electric signals. These electric signals are outputted as reception signals of ultrasonic waves.

Alternatively, as the ultrasonic transducers, plural kinds of elements of different ultrasonic conversion types may be used. For example, the above-mentioned vibrators are used as elements for transmitting ultrasonic waves and photo-detection type ultrasonic transducers are used as elements for receiving ultrasonic waves. The photo-detection type ultrasonic transducer is for detecting ultrasonic signals by converting the ultrasonic signals into optical signals, and configured by a Fabry-Perot resonator or fiber Bragg grating, for example.

The transmitting and receiving unit 20 includes a transmission circuit 21, a reception circuit 22, and an A/D converter 23. Further, the image generating section 30 includes a signal processing unit 31, a cine-memory 32, a B-mode image data generating unit 33, a speckle analysis unit 34, a DSC (Digital Scan Converter) 35, and a D/A converter 36.

The transmission circuit 21 generates drive signals to be respectively applied to the plural ultrasonic transducers 10a. At this time, the transmission circuit 21 can provide respective delay times to the drive signals based on the transmission delay pattern selected by the scan control unit 80. Here, the transmission circuit 21 may adjust the amounts of delay of the drive signals and supply the drive signals to the ultrasonic probe 10 such that the ultrasonic waves to be transmitted from the plural ultrasonic transducers 10a form an ultrasonic beam, or may supply drive signals to the ultrasonic probe 10 such that the ultrasonic waves to be transmitted at once from the plural ultrasonic transducers 10a reach the entire imaging region of the object.

The reception circuit 22 amplifies the reception signals respectively outputted form the plural ultrasonic transducers 10a, and the A/D converter 23 converts the analog reception signals amplified by the reception circuit 22 into digital reception signals (in this application, also referred to as "RF data"). The RF data outputted from the A/D converter 23 is inputted to the signal processing unit 31. The signal processing unit 31 performs reception focus processing by providing the respective delay times to the reception signals represented by the RF data based on the reception delay pattern selected by the scan control unit 80, and adding those reception signals to one another. Through the reception focus processing, sound ray data, in which the focal point of the ultrasonic echoes is stopped down, is formed.

The scan control unit 80 sequentially sets a transmission direction of an ultrasonic beam or a reception direction of ultrasonic echoes under the control of the control unit 60, and has a transmission control function for selecting a transmission delay pattern according to the set transmission direction and a reception control function for selecting a reception delay pattern according to the set reception direction.

Here, the transmission delay pattern refers to a delay time pattern to be provided to the drive signals in order to form an ultrasonic beam in a desired direction by using the ultrasonic waves transmitted from the plural ultrasonic transducers 10a, and the reception delay pattern refers to a delay time pattern to be provided to the reception signals in order to extract ultrasonic echoes from the desired direction by using the ultrasonic waves received by the plural ultrasonic transducers 10a. Plural transmission delay patterns and reception delay patterns are stored in a memory or the like.

Furthermore, the signal processing unit 31 corrects attenuation of the sound ray data due to distance in accordance with the depths of the reflection positions of ultrasonic waves through STC (sensitivity time gain control), and then, performs envelope detection processing by using a low-pass filter or the like thereon to generate envelope data.

The envelope data generated by the signal processing unit 31 is sequentially stored in the cine-memory 32 and supplied to the B-mode image data generating unit 33. The cine-memory 32 has a memory capacity for storing envelope data for at least one frame, preferably for plural frames. The B-mode image data generating unit 33 performs pre-process processing such as Log (logarithmic) compression and gain adjustment on the envelope data to generate B-mode image data, and outputs the generated B-mode image data to the DSC 35.

The speckle analysis unit 34 includes an envelope memory 341 and a computation part 342. When an operator operates a speckle analysis operation part 52 to instruct a speckle analysis, the envelope memory 341 stores the envelope data supplied from the signal processing unit 31 in the live mode, and stores the envelope data supplied from the cine-memory 32 in the freeze mode. The computation part 342 reads the envelope data from the envelope memory 341 and performs predetermined computation processing on the read envelope data to generate speckle analysis result data representing a speckle analysis result, and outputs the generated speckle analysis result data to the DSC 35.

In the embodiment, the computation part 342 is configured of a central processing unit (CPU) and software (data analysis program) for actuating the CPU to execute various kinds of processing. However, the computation part 342 may be configured of a digital circuit or analog circuit. Further, the signal processing unit 31, the B-mode image data generating unit 33, the DSC 35, the control unit 60, and the scan control unit 80 are also configured of a CPU and software. However, the signal processing unit 31, the B-mode image data generating unit 33, and the DSC 35 may be configured of a digital circuit or analog circuit. The above-mentioned software is stored in the storage unit 70 that is configured of a hard disk, memory, or the like. In addition, the transmission delay patterns and the reception delay patterns to be selected by the scan control unit 80 may be stored in the storage unit 70.

The DSC 35 converts (raster-converts) the B-mode image data into ultrasonic image data that follows the normal scan system of television signals, and performs necessary image processing such as gradation processing thereon to generate ultrasonic image data. Furthermore, the DSC 35 generates image data for display based on the ultrasonic image data. In addition, when the operator instructs the speckle analysis, the DSC 35 generates image data for display by synthesizing the ultrasonic image data and the speckle analysis result data in order to display the ultrasonic image and the speckle analysis result within one screen.

The D/A converter 36 converts the image data for display outputted from the DSC 35 into an analog image signal and outputs it to the display unit 40. Thereby, an ultrasonic diagnostic screen including the ultrasonic image and the speckle analysis result, if needed, is displayed on the display unit 40.

The input unit 50 includes a console 51 to be used for the operator to operate the ultrasonic diagnostic apparatus 1, and a speckle analysis operation part 52 as operator interface means for the operator to input instructions when the speckle analysis is performed.

Figure 2:
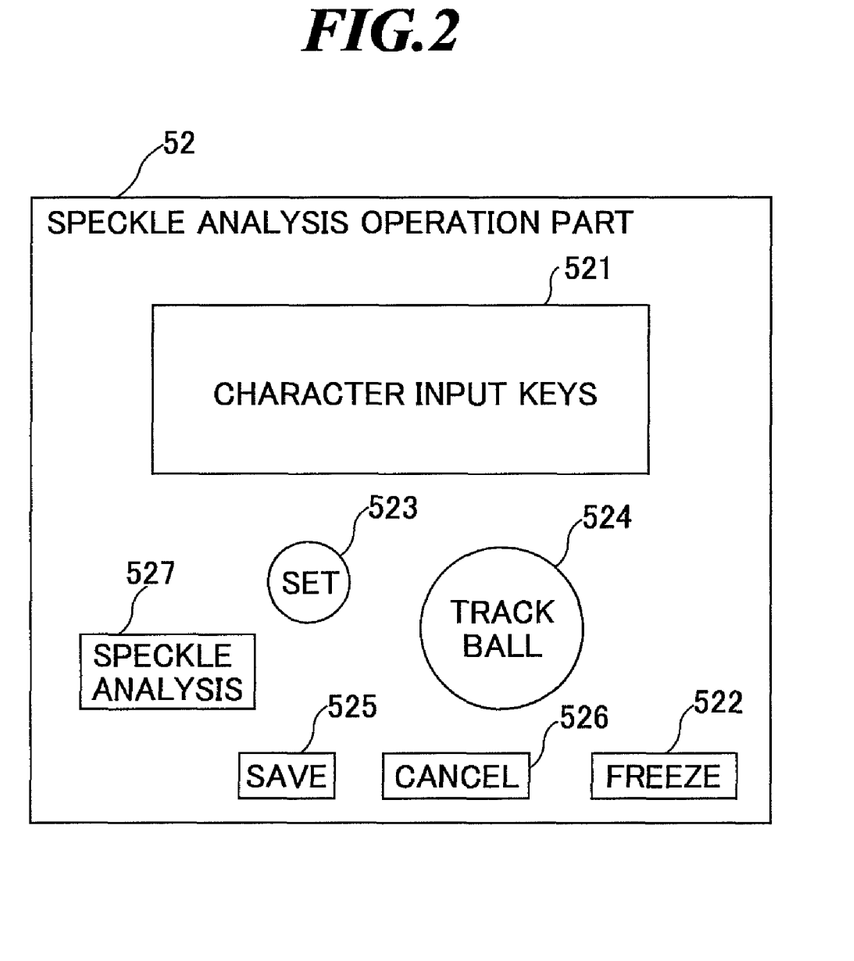
FIG. 2 shows an example of button arrangement in a speckle analysis operation part shown in FIG. 1.

FIG. 2 shows an example of button arrangement in a speckle analysis operation part shown in FIG. 1. In the embodiment, the speckle analysis operation part 52 is provided with character input keys 521 for inputting various kinds of instructions on data, a freeze button 522 for instructing switching between the live mode and freeze mode, a set button 523 for setting an ROI (region of interest) within an ultrasonic image, a track ball 524 for locating the ROI, a save button 525 for saving the ROI setting, a cancel button 526 for canceling the ROI setting, and a speckle analysis button 527 for instructing a speckle analysis. By pushing down these buttons, their instructions are informed to the control unit 60, and the control unit 60 controls the respective units.

In the ultrasonic diagnostic apparatus according to the embodiment, there are the live mode and the freeze mode, and the speckle analysis can be performed in both of the modes. Here, operations of the ultrasonic diagnostic apparatus in The respective modes will be explained with reference to FIGS. 1 to 3.

The live mode refers to a mode in which moving images are displayed based on the reception signals sequentially obtained through the transmission and reception of ultrasonic waves by the ultrasonic probe. In the live mode, ultrasonic image data is generated based on the envelope data outputted from the signal processing unit 31 based on the sequentially obtained reception signals. Concurrently, the cine-memory 32 sequentially stores the envelope data outputted from the signal processing unit 31.

During observation of moving images in the live mode, the operator is able to switch to the freeze mode and acquire a desired still image by pushing down the freeze button 522 shown in FIG. 2. Since the envelope data for at least one frame is stored in the cine-memory 32, in the freeze mode, ultrasonic image data is generated based on the envelope data read from the cine memory 32 without the need for imaging the object.

Hereinafter, an example of a procedure to perform a Speckle analysis in the freeze mode will be explained. First, in the live mode, the operator acquires a desired still image as an ultrasonic image by pushing down the freeze button 522 shown in FIG. 2.

Figure 3:
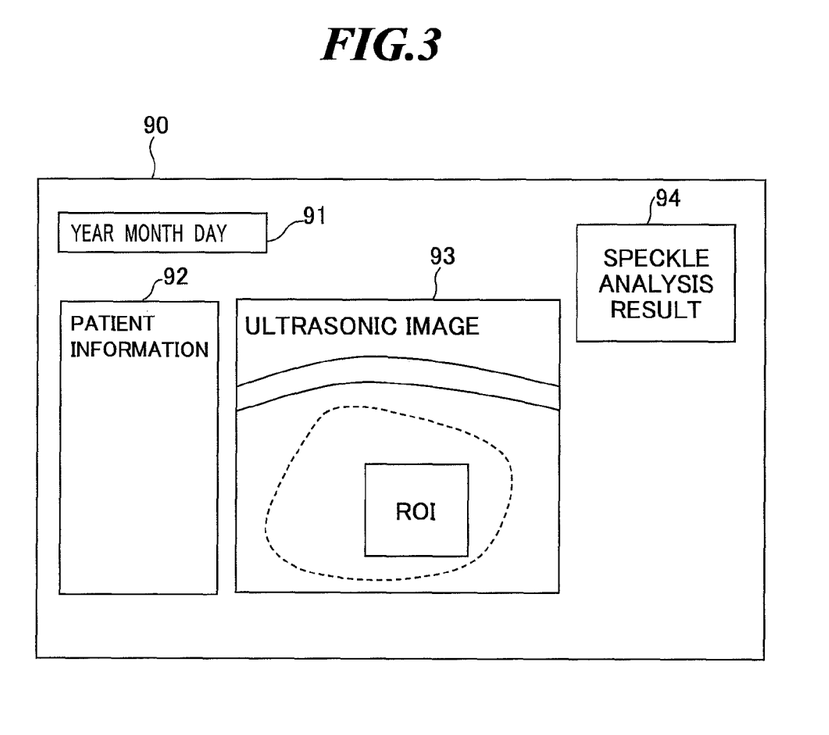
FIG. 3 shows an example of an ultrasonic diagnostic screen displayed on a display unit.

FIG. 3 shows an example of an ultrasonic diagnostic screen displayed on a display unit. An ultrasonic diagnostic screen 90 includes an examination date 91, patient information 92, an ultrasonic image 93, and a speckle analysis result 94. In the ultrasonic image 93, an ROI is indicated. The speckle analysis result 94 is displayed only when a speckle analysis is performed.

The operator pushes down the set button 523 shown in FIG. 2, and then searches for a position to be located as the ROI in the ultrasonic image by operating the track ball 524 and sets the ROI by pushing down the save button 525. Then, when the operator pushes down the speckle analysis button 527, a speckle analysis is performed in the speckle analysis unit 34.

When the speckle analysis button 527 is pushed down in the freeze mode, the envelope data of the same frame as the ultrasonic image frame displayed on the display unit 40 is read from the cine-memory 32 and stored in the envelope memory 341. Furthermore, the computation part 342 reads from the envelope memory 341 the envelope data corresponding to the same region as the ROI set in the ultrasonic image among a group of envelope data stored in the envelope memory 341.

The computation part 342 calculates histogram Hi(A) based on a value of the read envelope data, i.e., amplitude "A" of the envelope (hereinafter, also referred to as "brightness value") A, calculates probability density distribution P(A) based on the histogram Hi(A), and calculates Rayleigh distribution R(A) based on the probability density distribution P(A). In the case with no attenuation, the Rayleigh distribution R(A) can be expressed by the following equation (1).

$$R(A) = \frac{A}{\phi} \exp\left(-\frac{A^2}{2\phi}\right) \quad (1)$$

Here, the parameter (Rayleigh coefficient) $\phi$ in the equation (1) is a half of expectation $<A^2>$ of reception intensity and proportional to the reception intensity.

Furthermore, the computation part 342 calculates a value of the ratio P(A)/R(A) of the probability density distribution P(A) to the Rayleigh distribution.

Figure 4:
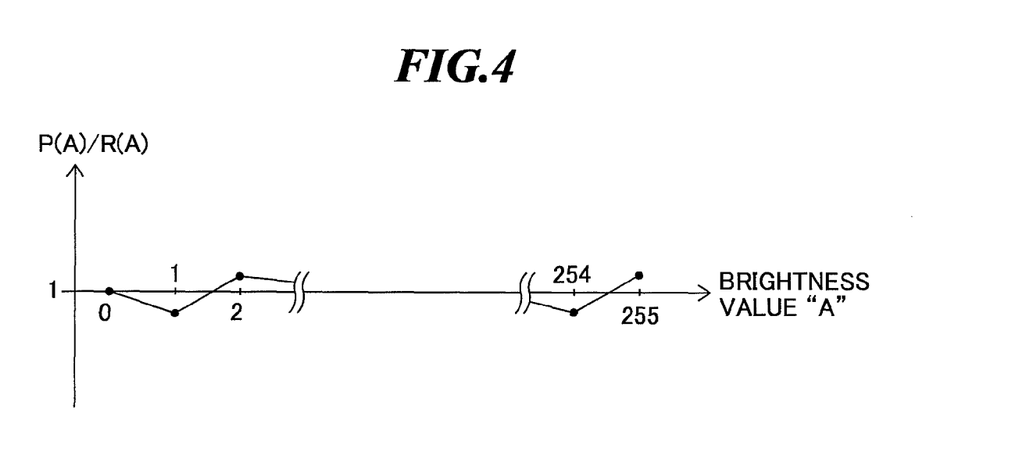
FIG. 4 shows values of the ratio of a probability density distribution to a Rayleigh distribution.

For example, if the envelope data is quantized with an accuracy of eight bits, the possible brightness value "A" is one of 0 to 255. FIG. 4 shows an example of values of the ratio P(A)/R(A) of the probability density distribution to the Rayleigh distribution. The computation part 342 calculates the mean value of P(A)/R(A) as parameter "K", and calculates the mean value of the absolute values of (1−P(A)/R(A)) as parameter "H". The parameter "K" is expressed by the equation (2), and the parameter "H" is expressed by the equation (3).

$$K = \text{Ave}\left(\frac{P(A)}{R(A)}\right) \quad (2)$$

$$H = \text{Ave}\left|1 - \frac{P(A)}{R(A)}\right| \quad (3)$$

Here, the parameter "K" represents the similarity between the probability density distribution P(A) and the Rayleigh distribution R(A), and the parameter "H" represents the degree of variations of the probability density distribution P(A) relative to the Rayleigh distribution R(A).

The probability density distribution P(A), the Rayleigh distribution R(A), and the parameters "K" and "H" are outputted to the DSC 35 as speckle analysis result data. The DSC 35 generates image data for display by synthesizing the ultrasonic image data and the speckle analysis data, and outputs the image data for display to the D/A converter 36. The D/A converter 36 converts the inputted image data for display into analog image signal and outputs it to the display unit 40.

Figure 5:
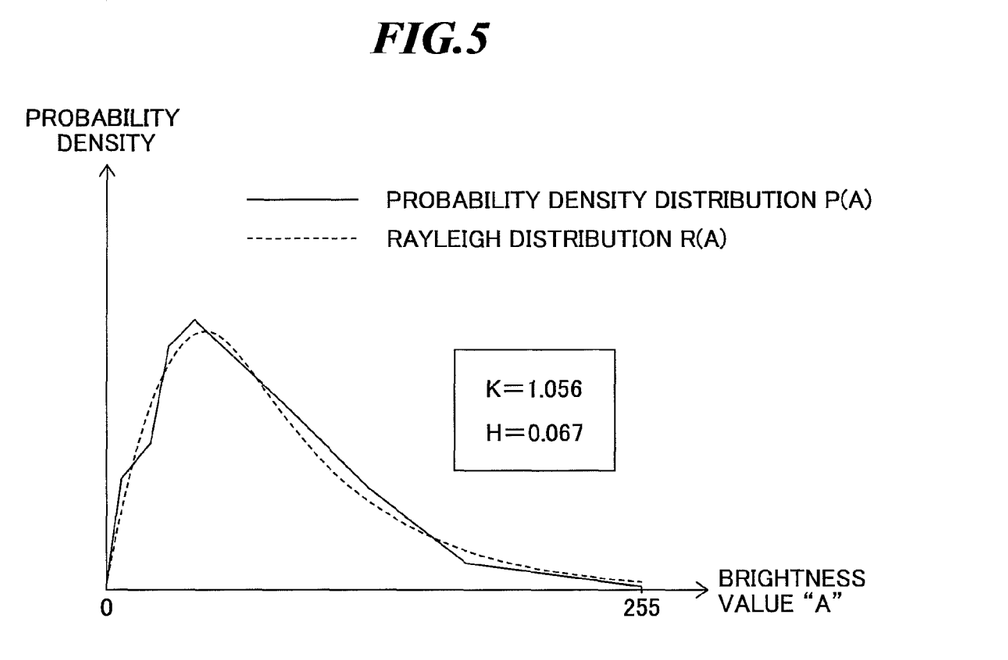
FIG. 5 shows an example of a speckle analysis result included in the ultrasonic diagnostic screen shown in FIG. 3.

FIG. 5 shows an example of a speckle analysis result included in the ultrasonic diagnostic screen shown in FIG. 3. As shown in FIG. 5, in the speckle analysis result, the probability density distribution P(A) obtained from the histogram of brightness "A" is indicated with the corresponding Rayleigh distribution R(A), and further, the values of the parameters "K" and "H" are also indicated. In FIG. 5, the solid line shows the probability density distribution P(A), and the broken line shows the Rayleigh distribution R(A).

Figure 6A:
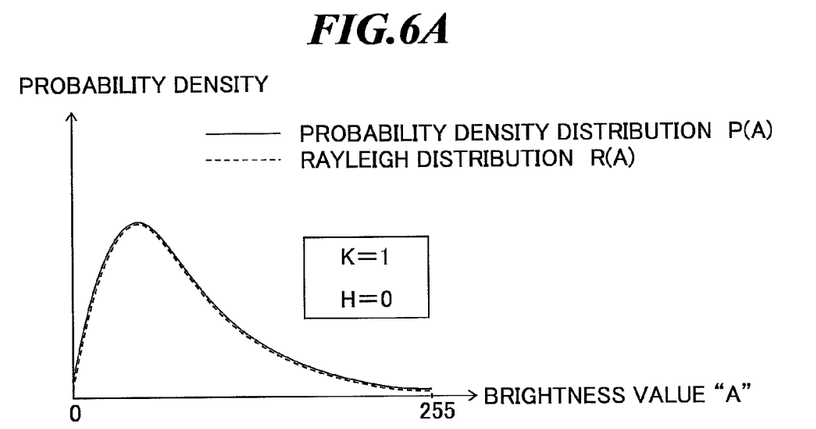
Figure 6B:
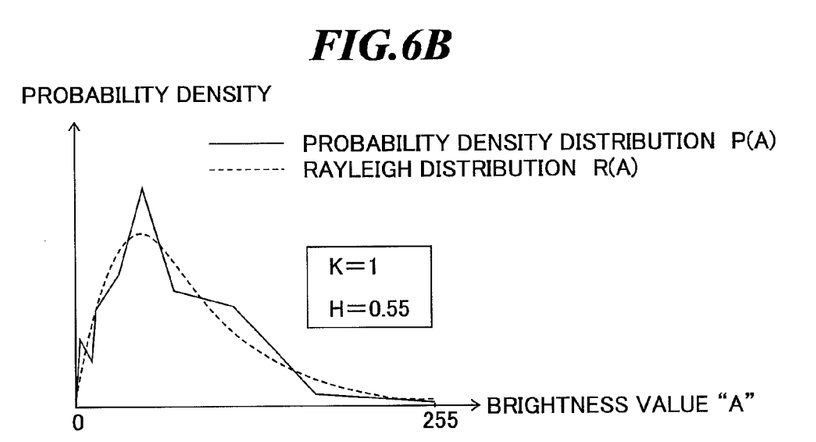
Figure 6C:
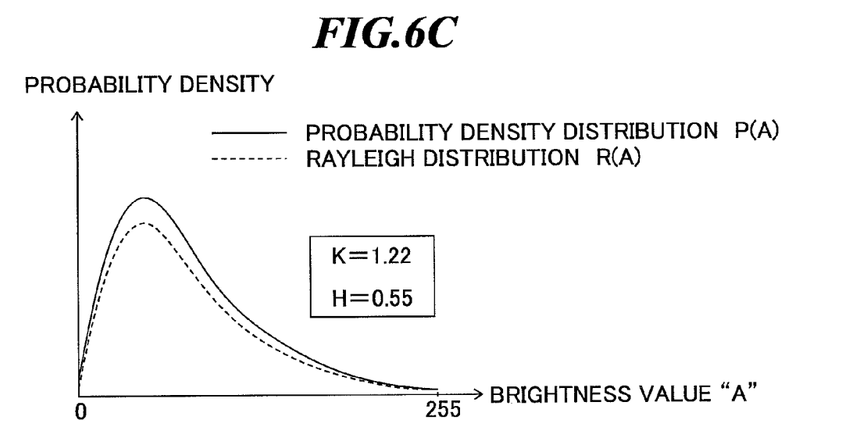

Next, information on tissue properties obtained based on the speckle analysis result will be explained with reference to FIGS.6A-6C. FIGS. 6A-6C show three examples of the speckle analysis result.

In FIG. 6(A), the probability density distribution P(A) obtained from the histogram is nearly conformable to the Rayleigh distribution R(A). In this case, the parameter "K" becomes nearly "1" and the parameter "H" becomes nearly "0", and the tissues of the liver and so on appearing in the ROI in the ultrasonic image are judged to be normal.

In FIG. 6B, the probability density distribution P(A) obtained from the histogram is like a line graph and deviates from the Rayleigh distribution R(A). In this case, the parameter "K" becomes nearly "1" and the parameter "H" becomes a value between "0" and "1", and it is judged that the number of samples is insufficient due to the small ROI. Accordingly, the operator can perform the speckle analysis again after the ROI is enlarged and the sufficient number of samples is secured.

In FIG. 6C, the probability density distribution P(A) obtained from the histogram is a smooth curve but deviates from the Rayleigh distribution R(A). In this case, the parameter "K" becomes larger than "1" and the parameter "H" becomes a value between "0" and "1", and the tissues of the liver and so on appearing in the ROI in the ultrasonic image are judged to have a hardened part. Therefore, for example, a diagnosis that it is suspected to have cirrhosis may be made.

In the above-mentioned operation, threshold value $T_K$ of the parameter "K" and threshold value TH of the parameter "H" may be set in advance and the judgment is automatically made by comparing these parameters with the respective threshold values. For example, given that the threshold values are set as $T_K$=1.15 and $T_H$=0.3, in the case where K≦$T_K$ and H≦$T_H$, the tissues may be judged to be normal, while in the case where H>$T_H$, the tissues may be judged to be abnormal if K>$T_K$, and the number of samples may be judged to be insufficient if K≦$T_K$.

According to the embodiment, when the operator sets an ROI based on an ultrasonic image in the live mode or freeze mode, it is possible to easily perform a speckle analysis on a desired part in the object and display the ultrasonic image and the corresponding speckle analysis result in real time.

Further, the operator may be able to arbitrarily set an arithmetic expression to be used when a Rayleigh distribution, parameters, and so on are calculated in the speckle analysis by operating the character input keys and so on of the speckle analysis operation part. For example, a speckle analysis with higher accuracy can be performed by setting an arithmetic expression that reflects frequency attenuation when the Rayleigh distribution is calculated. Alternatively, the operator may be able to set types of graphs and parameters to be displayed as a speckle analysis result.

Furthermore, when a speckle analysis result is displayed in the live mode, if the frame rate is high, the speckle analysis result is difficult to be read. Accordingly, the operator may be able to set the update rate at which the speckle analysis result is displayed on the display unit by operating the character input keys and so on of the speckle analysis operation part. Consequently, even when the frame rate of the ultrasonic image is high, the speckle analysis result can be easily read.

The invention claimed is:

1. An ultrasonic diagnostic apparatus comprising:
a transmitting and receiving unit for supplying drive signals to plural ultrasonic transducers respectively to transmit ultrasonic waves and converting reception signals, which are respectively outputted from said plural ultrasonic transducers receiving ultrasonic echoes, into digital signals;
a signal processing unit configured to perform reception focus processing and envelope detection processing on the digital signals to sequentially generate envelope data;
a storage unit configured to store the envelope data for at least one frame generated by said signal processing unit;
an image data generating unit configured to generate image data representing an ultrasonic image based on the envelope data supplied from one of said signal processing unit and said storage unit;
a speckle analyzing unit configured to generate speckle analysis result data representing a speckle analysis result based on the envelope data supplied from one of said signal processing unit and said storage unit, wherein said speckle analyzing unit includes a memory for storing the envelope data for at least one frame;
a display unit configured to display the ultrasonic image and the corresponding speckle analysis result based on the image data generated by said image data generating unit and the speckle analysis result data generated by said speckle analyzing unit;
an input unit configured to set a ROI (region of interest) in the ultrasonic image displayed on said display unit; and
a computation part configured to calculate a histogram, a probability density distribution, and a Rayleigh distribution on values of the envelope data corresponding to the ROI set by using said input unit among the envelope data stored in said memory, and further configured to calculate a mean value of P(A)/R(A) as a first parameter and a mean value of absolute values of (1-P(A)/R(A)) as a second parameter, where "A" represents a value of the envelope data, P(A) represents the probability density distribution, and R(A) represents the Rayleigh distribution, and to compare first and second parameters with respective threshold values to judge whether a tissue appearing in the ROI is normal or not and judge whether a number of samples is sufficient or not.

2. The ultrasonic diagnostic apparatus according to claim 1, wherein said input unit is also configured to set at least one of an arithmetic expression to be used by said computation part and a type of speckle analysis result to be displayed on said display unit.

3. The ultrasonic diagnostic apparatus according to claim 1, wherein said input unit is also configured to set an update rate at which the speckle analysis result is displayed on said display unit.

4. The ultrasonic diagnostic apparatus according to claim 1, wherein said memory stores at least the envelope data of the same frame as that of the ultrasonic image displayed on said display unit, and said computation part is configured to generate the speckle analysis result data based on the envelope data corresponding to the ROI set by using said input unit among the envelope data of the same frame as that of the ultrasonic image displayed on said display unit.

5. A data analysis method to be used in an ultrasonic diagnostic apparatus for supplying drive signals to plural ultrasonic transducers respectively to transmit ultrasonic waves and converting reception signals, which are respectively outputted from said plural ultrasonic transducers receiving ultrasonic echoes, into digital signals, said method comprising the steps of:
(a) performing reception focus processing and envelope detection processing on the digital signals to sequentially generate envelope data;
(b) storing the envelope data for at least one frame generated at step (a) in a storage unit;
(c) generating image data representing an ultrasonic image based on one of the envelope data generated at step (a) and the envelope data stored in said storage unit at step (b);
(d) displaying the ultrasonic image on a display unit based on the image data generated at step (c);

(e) setting a ROI (region of interest) in the ultrasonic image displayed on said display unit;

(f) storing the envelope data for at least one frame in a memory, calculating a histogram, a probability density distribution, and a Rayleigh distribution on values of the envelope data corresponding to the ROI set at step (e) among the envelope data stored in said memory, calculating a mean value of P(A)/R(A) as a first parameter and a mean value of absolute values of (1-P(A)/R(A)) as a second parameter, where "A" represents a value of the envelope data, P(A) represents the probability density distribution, and R(A) represents the Rayleigh distribution, and comparing the first and second parameters with respective threshold values to judge whether a tissue appearing in the ROI is normal or not and judge whether a number of samples is sufficient or not; and (g) displaying the ultrasonic image and the corresponding speckle analysis result on said display unit based on the image data generated at step (c) and the speckle analysis result data generated at step (f).

6. The data analysis method according to claim 5, further comprising the step of:

setting at least one of an arithmetic expression to be used at step (f) and a type of speckle analysis result to be displayed on said display unit.

7. The data analysis method according to claim 5, further comprising the step of:

setting an update rate at which the speckle analysis result is displayed on said display unit.

8. The data analysis method according to claim 5, wherein step (f) includes storing at least the envelope data of the same frame as that of the ultrasonic image displayed on said display unit in said memory, and generating the speckle analysis result data based on the envelope data corresponding to the ROI set at step (e) among the envelope data of the same frame as that of the ultrasonic image displayed on said display unit.

9. A data analysis program embodied on a non-transitory computer readable medium to be used in an ultrasonic diagnostic apparatus for supplying drive signals to plural ultrasonic transducers respectively to transmit ultrasonic waves and converting reception signals, which are respectively outputted from said plural ultrasonic transducers receiving ultrasonic echoes, into digital signals, said program actuating a CPU to execute the procedures of:

(a) performing reception focus processing and envelope detection processing on the digital signals to sequentially generate envelope data;

(b) storing the envelope data for at least one frame generated at procedure (a) in a storage unit;

(c) generating image data representing an ultrasonic image based on one of the envelope data generated at procedure (a) and the envelope data stored in the storage unit at procedure (b);

(d) displaying the ultrasonic image on a display unit based on the image data generated at procedure (c);

(e) setting a ROI (region of interest) in the ultrasonic image displayed on said display unit in accordance with operation of an operator;

(f) storing the envelope data for at least one frame in a memory, calculating a histogram, a probability density distribution, and a Rayleigh distribution on values of the envelope data corresponding to the ROI set at procedure (e) among the envelope data stored in said memory, calculating a mean value of P(A)/R(A) as a first parameter and a mean value of absolute values of (1-P(A)/R(A)) as a second parameter, where "A" represents a value of the envelope data, P(A) represents the probability density distribution, and R(A) represents the Rayleigh distribution, and comparing the first and second parameters with respective threshold values to judge whether a tissue appearing in the ROI is normal or not and judge whether a number of samples is sufficient or not; and (g) displaying the ultrasonic image and the corresponding speckle analysis result on said display unit based on the image data generated at procedure (c) and the speckle analysis result data generated at procedure (f).

10. The data analysis program according to claim 9, further actuating the CPU to execute the procedures of:

setting at least one of an arithmetic expression to be used at procedure (f) and a type of speckle analysis result to be displayed on said display unit.

11. The data analysis program according to claim 9, further actuating the CPU to execute the procedures of:

setting an update rate at which the speckle analysis result is displayed on said display unit.

12. The data analysis program according to claim 9, wherein procedure (f) includes storing at least the envelope data of the same frame as that of the ultrasonic image displayed on said display unit in said memory, and generating the speckle analysis result data based on the envelope data corresponding to the ROI set at procedure (e) among the envelope data of the same frame as that of the ultrasonic image displayed on said display unit.

* * * * *